ns Limited, Henrietta
United States Patent [19]

Harrison et al.

[11] 4,089,962
[45] May 16, 1978

[54] ACYLAMINO TRIAZOLES AS ANTIASTHMATIC AGENTS

[75] Inventors: Roger Garrick Harrison, Farnborough; William Boffey Jamieson, Woking; William James Ross, Lightwater; John Christopher Saunders, Maidenhead, all of England

[73] Assignee: Lilly Industries Limited, Henrietta Place, England

[21] Appl. No.: 691,963

[22] Filed: Jun. 1, 1976

[30] Foreign Application Priority Data

Jun. 5, 1975 United Kingdom ............... 24221/75

[51] Int. Cl.² ............................................. A61K 31/41
[52] U.S. Cl. .............................. 424/269; 260/239.3 R; 260/293.69; 424/267; 542/414; 542/421
[58] Field of Search .......... 260/308 R, 293.69, 240 R, 260/240 K, 308 A; 424/269, 267

[56] References Cited

U.S. PATENT DOCUMENTS

| 2,914,536 | 11/1959 | Hardy et al. | 260/308 |
| 2,953,491 | 9/1960 | Hardy et al. | 424/269 |

FOREIGN PATENT DOCUMENTS

| 698,428 | 11/1964 | Canada. |
| 2,164,234 | 7/1972 | Germany. |
| 1,111,680 | 5/1968 | United Kingdom. |

*Primary Examiner*—Raymond V. Rush
*Attorney, Agent, or Firm*—Nancy J. Harrison; Everet F. Smith

[57] ABSTRACT

1,2,3-triazoles and 1,2,4-triazoles having an N-substituted acylamino substituent are prepared by alkylating N-unsubstituted acylamino triazoles or acylating N-substituted amino triazoles. The N-substituted acylamino triazoles are useful as anti-allergy drugs. Pharmaceutical formulations containing acylamino triazoles and a method of treating allergic conditions utilizing such compounds are provided.

4 Claims, No Drawings

ACYLAMINO TRIAZOLES AS ANTIASTHMATIC AGENTS

This invention relates to heterocyclic chemical compounds and more particularly to certain novel 5-membered heteroaryl derivatives having nitrogen atoms as the sole heteroatoms in the ring, substituted by an acylamino group which are useful for the chemotherapy of immediate hypersensitivity conditions and/or which are useful as intermediates in preparing the active derivatives. The invention also includes processes for preparing the active compounds of the invention. Furthermore, the invention includes within its scope pharmaceutical compositions containing the pharmacologically active compounds and methods of treatment of animals, including humans, comprising administering thereto an effective dose of the compound or compounds or of pharmaceutical compositions comprising the active compound or compounds.

A number of acylamino derivatives of five membered heteroaryl systems similar to the compounds of the invention have been previously described - see for example United States Patent Specification No. 3,557,137. However, it is to be noted that such prior disclosures of this type of compound have either disclosed a utility quite different from that possessed by the compounds of the invention or have been publications of academic interest only in which no utility whatsoever has been disclosed.

According to the present invention there is provided a novel heteroaryl derivative of the formula:

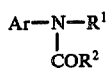   (I)

wherein Ar represents an optionally substituted triazolyl group, the acylamino group —NR$^1$COR$^2$ being attached to a carbon atom of the triazolyl ring, R$^1$ is C$_{1-10}$ alkyl, C$_{3-6}$ alkenyl, C$_{3-6}$ alkynyl, C$_{2-6}$ alkoxyalkyl, C$_{2-6}$ carboxyalkyl, C$_{1-6}$ haloalkyl, C$_{3-10}$ cycloalkyl, C$_{3-10}$cycloalkyl-C$_{1-6}$ alkyl, optionally substituted phenyl-C$_{1-6}$ alkyl or optionally substituted phenyl-C$_{2-6}$ alkenyl; and R$^2$ is C$_{1-8}$ alkyl, C$_{1-6}$ haloalkyl, C$_{2-6}$ alkenyl, C$_{3-10}$ cycloalkyl, C$_{3-10}$ cycloalkyl-C$_{1-6}$ alkyl, optionally substituted phenyl, optionally substituted phenyl-C$_{1-6}$ alkyl, optionally substituted phenyl-C$_{2-6}$ alkenyl, C$_{1-4}$ alkoxycarbonyl-C$_{1-8}$ alkyl, C$_{2-8}$ carboxyalkyl or C$_{3-6}$ acyloxyalkyl; or R$^1$ and R$^2$ together form a lactam ring having 5 to 7 ring atoms; provided that:

Ar cannot be 1,2,4-triazolyl substituted by a heteroaryl, alkylamino or C$_2$ alkenyl group.

The heteroaryl nucleus is preferably substituted by one or two groups selected from C$_{1-4}$ alkyl, benzyl, phenyl and halogen.

Preferred R$^1$ substituents are C$_{1-10}$ alkyl, C$_{3-6}$ alkenyl, C$_{3-8}$ cycloalkyl, and benzyl optionally substituted by halogen. Preferred R$^2$ substituents are C$_{1-8}$ alkyl, C$_{2-6}$ alkenyl, C$_{3-10}$ cycloalkyl, phenyl, benzyl, C$_{1-4}$ alkoxycarbonyl-C$_{4-8}$ alkyl, C$_{2-8}$ carboxyalkyl and C$_{3-6}$ acyloxyalkyl.

The term "C$_{1-6}$ alkyl" as used herein means a straight or branched chain alkyl group containing from 1 to 6 carbon atoms such as methyl, ethyl, isopropyl, n-butyl, s-butyl, isobutyl, t-butyl, n-amyl, s-amyl, n-hexyl, 2-ethylbutyl or 4-methylamyl.

Similarly the term "C$_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl. "C$_{1-4}$ hydroxyalkyl" and "C$_{3-6}$ acyloxyalkyl" mean the aforementioned C$_{1-4}$ alkyl groups substituted with an hydroxy group and acyloxy group respectively. "C$_{2-6}$ alkoxyalkyl" and "C$_{1-6}$ haloalkyl" mean the aforementioned C$_{1-6}$ alkyl groups substituted with an alkoxy group or one or more halogen atoms, such as methoxyethyl, ethoxyethyl, ethoxybutyl, dibromoethyl, trifluoromethyl, 1-chloroethyl, 1,1-dichloroethyl, 1-iodobutyl or pentafluoroethyl.

The term "C$_{3-6}$ alkynyl" is used herein to indicate an alicyclic hydrocarbon group having 3 to 6 carbon atoms which contains a —C≡C—group. However, it should be noted that the —C≡C— group cannot be directly adjacent the nitrogen atom of the acylamino group. Similarly, C$_{3-6}$ alkenyl groups may not contain a —C≡C— group directly adjacent the nitrogen atom.

"C$_{3-10}$ cycloalkyl" means a saturated ring having from 3 to 10 carbon atoms in the ring as cyclopropyl, cyclobutyl, cyclopentyl, cyclooctyl, or adamantyl. "C$_{3-10}$ cycloalkyl-C$_{1-6}$ alkyl" means the aforementioned saturated rings attached to a C$_{1-6}$ alkylene bridge.

The term "optionally substituted phenyl" as used herein means a phenyl group unsubstituted or substituted by one or more groups which do not substantially alter the pharmacological activity of the compounds of formula (I), such as halogen, trifluoromethyl, methyl, methoxy, or nitro groups.

The term "C$_{2-6}$ carboxyalkyl" as used herein means a C$_{1-5}$ alkyl group substituted by a carboxylic acid group. Examples of such groups are carboxymethyl, carboxyethyl, carboxypropyl and carboxybutyl.

The triazolyl groups embraced within the scope of the invention are 1,2,3-triazolyl and 1,2,4-triazolyl. 1,2,4-Triazolyl is presently preferred.

Preferred 1,2,4-triazoles of the invention are those having the structural formula:

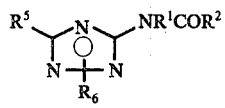   (III)

where R$^5$ indicates an optional substituent selected from formyl, carboxyl, hydroxy, C$_{1-4}$ hydroxyalkyl, C$_{1-4}$ alkyl, C$_{3-10}$ cycloalkyl, C$_{3-6}$ acyloxyalkyl, optionally substituted phenyl and halogen and R$^6$ indicates a substituent on one of the nitrogen atoms selected from hydrogen, C$_{1-4}$ alkyl and optionally substituted phenyl.

Particularly interesting triazoles of formula (III) are those in which R$^1$ is C$_{1-4}$ alkyl or benzyl optionally substituted by halogen and R$^2$ is C$_{1-6}$ alkyl, C$_{3-6}$ cycloalkyl, phenyl or benzyl. Compounds of formula (I) as defined above may be prepared by:

(a) acylating an alkyl derivative of formula:

   (V)

where Ar and R$^1$ are as defined previously; or (b) alkylating an acyl derivative of formula:

   (VI)

where Ar and R$^2$ are as defined previously.

The acylation of the compound of formula (V) may be carried out with an acid halide having the formula $R^2CO-X$ wherein X is chlorine or bromine and $R^2$ is defined above. Although acylation may be carried out in the presence of a proton acceptor, such as pyridine or triethylamine, in an inert solvent, such as benzene, no proton acceptor or solvent is required, it generally being preferred to accomplish the acylation using the acid halide at elevated temperatures.

The acylation may also be carried out by heating the alkyl derivative of formula (V) with a suitable acid anhydride, $(R^2CO)_2O$, in an inert solvent.

When alkyl derivatives of formula (V) are acylated in which Ar is a heteroaryl nucleus wherein the ring nitrogen atoms are unsubstituted or substituted only by hydrogen, there is a possibility of acylation of a ring nitrogen atom as well as the exocyclic amino group $NHR^1$. In such cases, if desired, the acyl group may be removed from the ring by hydrolysis which occurs preferentially at the ring nitrogen atom.

Those skilled in the art will immediately appreciate that a wide variety of other acylating conditions can be used (see, for example, "The Chemistry of Amides" 1971 by A. J. Beckwith; "Survey of Organic Synthesis", 1970 by Buehler and Pearson; "Organic Functional Group Preparations" 1968 by Sandler and Karo; "Reagents for Organic Synthesis" 1968 by Fieser and Fieser, etc.).

Compounds of formula (VI) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula $R^1X^1$ where $X^1$ is a reactive atom such as a halogen atom or a reactive group such as an alkyl sulphate group.

Of course, alkylating agents and alkylating reaction conditions other than those specified above can be utilised, the nature of these being readily apparent to those acquainted with the art.

Alkylation of compounds of formula (VI) in which the ring nitrogen atoms are unsubstituted may lead to the formation of mixtures of alkylated products which in certain circumstances may be difficult to separate.

The derivatives of formula (V) and (VI) can be derived from the corresponding amines of formula $ArNH_2$ by standard alkylation or acylation techniques.

The amines of formula $ArNH_2$ are either known compounds, see, for example, *Chemical Reviews,* 61 87 (1961) and *Chemische Berichte,* 97, 396 (1964), or can be prepared by modification of known synthetic methods.

The intermediates of formula (VI) except when Ar is a 1,2,4-triazolyl group and $R^2$ is methyl or phenyl are novel and are provided in a further aspect of the invention.

Compounds of formula (I) have been shown to be useful in the prophylactic and therapeutic treatment of immediate hypersensitivity diseases including asthma and in the alleviation of *status asthmaticus.* The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression, "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of thoobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminum, magnesium or calcium stearates, talc or mineral oil.

The following Examples will further illustrate the invention.

EXAMPLE 1

N-Methyl-N-[3-phenyl-1(H)-1,2,4-triazol-5-yl]heptanamide (a) 1-Heptanoyl-3-phenyl-5-methylamino-1 (H)-1,2,4-triazole 3-Methylamino-5-pheny-1(H)-1,2,4-triazole (8.7 g) and heptanoic anhydride (13.5 ml) in toluene (150 ml) were heated under reflux for 4 hours. The toluene was distilled off, and the resulting oil was crystallised from ethanol/water to give the title compound (12.0 g).

Analysis: $C_{16}H_{22}N_4O$ requires: C 67.12; H 7.74; N 19.25%. found: C 67.05; H 7.72; N 19.25%.

(b) N-Methyl-N-[3-phenyl-1(H)-1,2,4-triazol-5-yl]heptanamide

1-Heptanoyl-3-phenyl-5methylamino-1(H)-1,2,4-triazole (5.0 g) and heptanoic anhydride (10 ml) were heated under reflux for 2 hours. On cooling, the mixture was poured into a 10% sodium carbonate solution (200 ml), and ethanol (100 ml) was added. After stirring one hour, this mixture was extracted with diethyl ether (3 × 200 ml) which was then evaporated to an oil. The oil was dissolved in methanol (100 ml) and sodium hydroxide (8.0 g) was added and the solution stirred for two hours at room temperature. The methanol was distilled off, and the resulting oil was dissolved in water, filtered, and the filtrate acidified with acetic acid, whereupon a white solid separated. This was filtered off, washed, dried and recrystallised from ethyl acetate to give the title compound (3.4 g) m.p. 170° C.

EXAMPLE 2

N-Methyl-N-[3-phenyl-1(H)-1,2,4-triazol-5-yl]cyclopropane carboxamide

3-Methylamino-5-phenyl-1(H)-1,2,4-triazole (3.5 g) and cyclopropane carboxylic acid chloride (10.5 g) were added to toluene (50 ml) and heated under reflux for 4 hours. Then more cyclopropanecarboxylic acid chloride (5.3 g) was added and the heating continued for a further 18 hours. The solution was evaporated to an oil which was crystallised from 60°–80° C petrol with charcoaling to give a white solid (2.7 g). This solid (1.6 g) was dissolved in methanol (25 ml) and sodium hydroxide (1.0 g) added and the solution stirred for 2 hours at room temperature, and then the methanol was distilled off. The residue was taken up in water (20 ml) and acidified with glacial acetic acid, whereupon a white solid separated (1.1 g). This was recrystallised from ethylacetate/(60°–80° C.) petrol and then from ethanol/water to give the title compound (0.6 g) m.p. 169° C.

EXAMPLE 3

N-(3-Phenyl-1(H)-1,2,4-triazol-5-yl)butanamide

3-Amino-5-phenyl-1(H)-1,2,4-triazole (20 g) was stirred and heated to reflux with butyric anhydride (100 ml) for 2 hours. The excess anhydride was removed by distillation under reduced pressure. The oil obtained was triturated with petrol to give a solid which was recrystallised from ethanol to give a cream solid (21 g). The structure was confirmed by spectral data, e.g. N.M.R. spectra.

EXAMPLES 4 – 6

The following compounds were similarly prepared and characterised.

N-(3-Phenyl-1(H)-1,2,4-triazol-5-yl)-acetamide (m.p. 201°–203° C.)

White crystalline solid (from petrol ether (40°-60° C)/ethyl acetate)

N-(3-Methyl-1(H)-1,2,4-triazol-5-yl)butanamide (m.p. 252°–254° C).

Off-white crystalline solid.

EXAMPLE 7

N-(3-Phenyl-1(H)-1,2,4-triazol-5-yl)butylamine

N-(3-Phenyl-1(H)-1,2,4-triazol-5-yl)butanamide (10 g) in freshly distilled (from $LiAlH_4$) THF (200 ml) was added to a stirred suspension of lithium aluminum hydride (3.5 g) in freshly distilled THF (30 ml) under a nitrogen atmosphere. The reaction was stirred and heated to reflux for 2 hours then cooled and a solution of water (3.5 ml) in THF (3.5 ml) added dropwise followed by 2N NaOH (3.5 ml) followed by water (7 ml). The reaction mixture was filtered through a supercel pad and the solution evaporated to dryness under reduced pressure. The residue was crystallised from ethyl acetate/ether to give a white crystalline solid m.p. 168°–169° C. N.M.R. data was in full accord with the expected structure.

EXAMPLES 8 AND 9

The following compounds were similarly prepared and characterised.

N-(3-Phenyl-1(H)-1,2,4-triazol-5-yl)ethylamine (m.p. 191°–193°C.)

Yellow solid.

N-(3-Methyl-1(H)-1,2,4-triazol-5-yl)butylamine (m.p. 160°–161° C.)

White solid (from water).

EXAMPLE 10

N-Butyl-N-[3-phenyl-1(H)-1,2,4-triazol-5-yl]butanamide

3-Butylamino-5-phenyl-1(H)-1,2,4-triazole (0.5 g) and butanoyl chloride (5 ml) were heated under reflux, under nitrogen, for 18 hours. The volatile material was then distilled off, and the resulting oil stirred with sodium hydroxide (1.0 g) in methanol (10 ml) at room temperature for one hour. The solvent was evaporated off, and the residue dissolved in water, filtered, and the filtrate acidified with glacial acetic acid to give a white solid. This solid was recrystallised with charcoaling, from ethanol/water to give the title compound. (0.34 g). m.p. 113.5°–114° C.

EXAMPLES 11 AND 12

The following compounds were similarly prepared:

N-Ethyl-α-methyl-N-[3-phenyl-1(H)-1,2,4-triazol-5-yl]propanamide. m.p. 120°–121° C.

N-Butyl-N-[3-phenyl-1(H)-1,2,4-triazol-5-yl]-benzene acetamide (m.p. 120°–122° C)

EXAMPLE 13

N-Benzyl-N-[3-methyl-1(H)-1,2,4-triazol-5-yl]heptanamide (a) 3-Benzylamino-5-methyl-1(H)-1,2,4-triazole 3-Amino-5-methyl-1(H)-1,2,4-triazole (1.0 g) and benzaldehyde (10 ml) were dissolved in ethanol (50 ml), and the solution was heated under reflux for ½ hour. Sodium borohydride (2.0 g) and ethanol (50 ml) were then added and the heating continued a further ½ hour. The suspension was poured into water (300 ml), from which the organic material was extracted with ethyl acetate (3 × 100 ml). On evaporation of the solvent an oil was obtained, and this, on trituration with diethyl ether gave the title compound as a white solid, (1.3 g) m.p. 173° C.

(b) 3-Benzylamino-5-methyl-1(H)-1,2,4-triazole (1.9 g) was acylated by the method described in Example 2 with heptanoyl chloride (10 ml) to give the title compound as a colourless oil. Mass spectral data confirmed the structure of the product.

EXAMPLE 14

N-[4-Butyl-3-methyl-4(H)-1,2,4-triazol-5-yl]-α-methylpropanamide (a) 1-Amino-3-butylguanidinehydroiodide S-Methylisothiosemicarbazide hydroiodide (46.6 g) and 1-aminobutane (48 ml) and water (100 ml) were heated under reflux for 1 hour. The resulting solution was evaporated to an oil which was crystallised from amyl alcohol/80-100 PE, to give the title compound (a).

(b) 3-Amino-4-butyl-5-methyl-4(H)-1,2,4-triazole

1-Amino-3-butylguanidine hydroiodide (10.3 g) and acetic acid (20 ml) were heated under reflux for 48 hours and then evaporated to give a viscous oil. This oil was treated with aqueous sodium carbonate and the resulting solution was evaporated to dryness. This solid was extracted with ethyl acetate and the soluble fraction was again evaporated to dryness. The residue was extracted with toluene, and subsequently with chloroform. Evaporation of the chloroform fraction, followed by crystallisation from ethyl acetate/ethanol gave the title compound (b) (1.4 g) m.p. 200° C.

(c) N-[4-Butyl-3-methyl-4(H)-1,2,4-triazole]-α-methylpropanamide

3-Amino-4-butyl-5-methyl-4(H)-1,2,4-triazole(1.3 g) and isobutyric anhydride (20 ml) were heated together under reflux for 18 hours in a nitrogen atmosphere and then evaporated to dryness to give the title compound as an oil. The NMR spectrum was consistent with the assigned structure.

EXAMPLES 15 – 17

N-[1,4-Diphenyl-1(H)-1,2,3-triazol-5-yl]-N-propyl acetamide

N-[1,4-Diphenyl-1(H)-1,2,3-triazol-5-yl]acetamide was alkylated with 1-iodopropane in the presence of sodium hydride in dimethyl-formamide to give the title compound.

Similarly prepared were:
N-[1,4-Diphenyl-1(H)-1,2,3-triazol-5-yl]-N-methylcyclopropane - carboxamide and
N-[1,4-Diphenyl-1(H)-1,2,3-triazol-5-yl]-N-benzylheptanamide

EXAMPLES 18–20

N-Butyl-N-[2-phenyl-2(H)-1,2,3-triazol-4-yl]-2-methylpropionamide

4-Amino-2-phenyl-2(H)-1,2,3-triazole was acylated with isobutyric acid and the resulting amide alkylated as in the above examples to give the title compound.

Similarly prepared was N-Butyl-N-[1-methyl-1(H)-1,2,3-triazol-5-yl] cyclopentane carboxamide from the corresponding amine (5-amino-1-methyl-1(H)-1,2,3-triazole) and N-Butyl-N-[5-methyl-1-phenyl-1(H)-1,2,3-triazol-4-yl]-acetamide from the corresponding amine (4-amino-5-methyl-1-phenyl-1-phenyl-1(H)-1,2,3-trizole).

EXAMPLES 21–23

The following compounds were prepared in a similar manner to that described in Example 10.
N-Butyl-N-(3-methyl-1(H)-1,2,4-triazol-5-yl)-2-methylpropionamide (m.p. 92.5°–4° C)
N-Butyl-N-(3-phenyl-1(H)-1,2,4-triazol-5-yl)-cyclohexane carboxamide (m.p. 110.5°–112° C)
N-Butyl-N-(3-phenyl-1(H)-1,2,4-triazol-5-yl)-2-methylpropanamide - gum, structure supported by NMR. (M/e 286).

EXAMPLES 24–26

Similarly, using the procedure described in Example 13 there were prepared:
N-(4-Chlorobenzyl)-N-[3-methyl-1(H)-1,2,4-triazol-5-yl]acetamide (m.p. 124° C)
N-(4-Chlorobenzyl-N-[3-methyl-1(H)-1,2,4-triazol-5-yl]benzamide (M/e 326/8)
N-(4-Chlorobenzyl)-N-[3-methyl-1(H)-1,2,4-triazol-5-yl]cyclohexanecarboxamide (m.p. 143° C).

EXAMPLES 27–28

Further, using the procedure of Example 1 there was prepared:
N-methyl-N-[3-phenyl-1(H)-1,2,4-triazol-5-yl]-benzamide (m.p. 147° C)
Using the procedure of Example 10 but using acetyl bromide, was prepared:
N-methyl-N-[3-phenyl-1(H)-1,2,4-triazol-5-yl]acetamide (m.p. 196° C)

EXAMPLES 29–30

N-Methyl-N-(1-methyl-5-phenyl-1,2,4-triazol-3-yl)-heptanamide and
N-Methyl-N-(1-methyl-3-phenyl-1,2,4-triazol-5-yl)-heptanamide N-Methyl-N-(3-phenyl-1(H)-1,2,4-triazol-5-yl)heptanamide (8.6 g) was added to a stirred solution of sodium (0.69 g) in ethanol (100 ml). Iodomethane (2.5 ml) was then added and the mixture stirred for 18 hours. The mixture was then evaporated to dryness and partitioned between water and ether. The ether fraction was dried and evaporated to give a mixture of N-methyl-N-(1-methyl-5-phenyl-1,2,4-triazol-3-yl)-heptanamide and N-methyl-N-(1methyl-3-phenyl-1,2,4-triazol-5-yl)-heptanamide which was separated into its two components by distillation, crystallisation and preparative thin-layer chromatography. The two components were distinguished and identified by N.M.R. The N-methyl-N-(1-methyl-5-phenyl-1,2,4-triazol-3-yl)-heptanamide was liquid at room temperature and had an $\eta_D^{22} = 1.5420$. The N-methyl-N-(1-methyl-3-phenyl-1,2,4-triazol-5-yl)-heptanamide was crystalline and had a melting point of 75°–77° C.

EXAMPLE 31

The amide of Example 14 was butylated with n-butylbromide to give N-n-butyl-N-[4-butyl-3-methyl-4(H)-1,2,4-triazole]-α-methylpropanamide.

The following Examples 32-38 illustrate pharmaceutical formulations containing the active compound N-benzyl-N-[3-methyl-1(H)-1,2,4-triazol-5-yl]heptanamide.

EXAMPLE 32

Soft gelatin capsules were prepared using the following ingredients:

|  | Quantity (mg/capsule) |
|---|---|
| Active compound | 25 |
| Propyl gallate | 0.04 |
| Fractionated Coconut Oil B.P.C. | 70 |

The above ingredients were mixed and filled into soft gelatin capsules, the main shell components of which were gelatin and glycerine.

EXAMPLE 33

Hard gelatin capsules were prepared using the following ingredients:

|  | Quantity(mg/capsule) |
|---|---|
| Active compound | 25 |
| Silicon dioxide (fumed) | 25 |
| Lactose | 60 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 34

An ointment was made up from the following ingredients:

| Active compound | 1.8% by weight |
|---|---|
| Butylated hydroxyanisole B.P. | 0.04% by weight |
| White soft paraffin | q.s. 100% |

The hydroxyanisole was dissolved in the melted paraffin and the active compound then added in, and the mixture allowed to cool.

EXAMPLE 35

A topical cream containing 1% of the compound was prepared as follows:

|  | grams: |
|---|---|
| Active compound | 1 |
| Cetomacrogol 1000 | 3 |
| Cetostearyl alcohol | 12 |
| Liquid Paraffin | 7 |
| Butylated hydroxyanisole B.P. | 0.04 |
| Distilled Water | to 100.0 |

The active compound was mixed with the hydroxyanisole and suspended in the liquid paraffin. The cetostearyl alcohol was added and the mixture heated to 70° C. with stirring. The cetomacrogol 1000 was then dissolved in 60 g. of water heated to 70 C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 36

Suppositories containing 30 and 60 mg. of the compound were prepared as follows:-

| Active compound | 3 g |
|---|---|
| Henkel base | 97 g |

The active compound was mixed with the Henkel base which had been previously melted using the minimum amount of heat possible. The mixture was then poured into suppository moulds of a nominal capacity of 1 g. or 2 g. as desired, to produce suppositories each containing 30 mg. or 60 mg. of the active compound.

EXAMPLE 37

An aerosol was prepared containing the following ingredients:-

|  | Quantity per ml. |
|---|---|
| Active compound | 10.00 mg. |
| Propylene glycol | 10.00 mg. |
| Dichlorotetrafluoroethane (Propellant 114) | 470 mg. |
| Dichlorodifluoromethane (Propellant 12) | 930 mg. |

The active compound was mixed with the propylene glycol and the mix added to the propellant 114, the mixture cooled to $-15°$ to $-20°$ C. and transferred to a filling device. At the same time a mixture of propellants 114 and 12, previously cooled to $-15$ to $-20°$ C. was fed into a second filling device. A metered amount of propellant from the second filling device was introduced into a stainless steel container, followed by the required amount of material from the first filling device. The valve units were then fitted and sealed to the container. These valve units were equipped with metering device so that approximately 0.15 mg. of the active compound is released by a single actuation of the valve.

EXAMPLE 38

Tablets were prepared using the following components:

| Active compound | 15.00 mg. |
|---|---|
| Microcrystalline Cellulose | 240.00 mg. |
| Sodium Carboxymethyl Starch | 22.00 mg. |
| Magnesium Stearate | 2.5 mg. |
| Butylated Hydroxyanisole B.P. | 0.002 mg. |

The hydroxyanisole was dissolved in the active compound, the solution adsorbed onto the microcrystalline cellulose. This was mixed with the sodium carboxymethyl starch and the magnesium stearate then mixed in. Finally, the mixture was compressed to form tablets.

We claim:

1. An anti-asthma treatment method which comprises administering to a mammal suffering from an asthmatic condition and in need of treatment, an amount of a compound of the following formula effective to alleviate said asthmatic condition:

wherein Ar represents an unsubstituted triazolyl group or a triazolyl group substituted by one or two groups selected from the group $C_{1-4}$ alkyl, benzyl, phenyl, and halogen; the acylamino group -$NR^1COR^2$ being attached to a carbon atom of the triazolyl ring, $R^1$ when taken separately is $C_{1-10}$ alkyl, $C_{3-6}$ alkenyl $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, phenyl-$C_{2-6}$ alkenyl, or substituted phenyl $C_{1-6}$ alkyl and substituted phenyl-$C_{2-6}$ alkenyl wherein said phenyl substituent can be halogen, trifluoromethyl, methyl, methoxy or nitro; and $R^2$ when taken separately is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, $C_{1-4}$ alkoxycarbonyl-$C_{1-8}$ alkyl, $C_{2-8}$ carboxyalkyl, phenyl, phenyl-$C_{1-6}$ alkyl, phenyl-$C_{2-6}$ alkenyl, substituted phenyl, substituted phenyl-$C_{1-6}$ alkyl or substituted phenyl-$C_{2-6}$ alkenyl wherein the said substituent can be halogen, trifluoromethyl, methyl, methoxy or nitro or $R^1$ and $R^2$ together form a lactam ring having 5 to 7 ring atoms.

2. An anti-asthma treatment method which comprises administering to a mammal suffering from an asthmatic condition and in need of treatment, an amount of a compound of the following formula effective to alleviate said asthmatic condition:

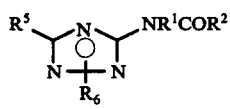

where
$R^1$ is $C_{1-4}$ alkyl, benzyl, or benzyl substituted with halogen; $R^2$ is $C_{1-6}$ alkyl, $C_{3-6}$ cycloalkyl, phenyl, or benzyl; $R^5$ is hydrogen, formyl, carboxyl, hydroxy, $C_{1-4}$ hydroxyalkyl, $C_{1-4}$ alkyl, $C_{3-10}$ cycloalkyl, halogen, phenyl, or substituted phenyl wherein said substituent can be halogen, trifluoromethyl, methyl, methoxy or nitro; and
$R^6$ indicates a substituent on one of the nitrogen atoms selected from hydrogen, $C_{1-4}$ alkyl, phenyl and substituted phenyl wherein said substituennts can be halogen, trifluoromethyl, methyl, methoxy or nitro.

3. A pharmaceutical formulation for the treatment of asthma consisting of, in unit dosage form, a pharmaceutical carrier and as the therapeutic agent from 5 to 500 mg. of a compound of the formula

wherein Ar represents an unsubstituted triazolyl group or a triazolyl group substituted by one or two groups selected from the group $C_{1-4}$ alkyl, benzyl, phenyl, and halogen; the acylamino group -$NR^1COR^2$ being attached to a carbon atom of the triazolyl ring, $R^1$ when taken separately is $C_{1-10}$ alkyl, $C_{3-6}$ alkenyl $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, phenyl-$C_{2-6}$ alkenyl, or substituted phenyl $C_{1-6}$ alkyl and substituted phenyl-$C_{2-6}$ alkenyl wherein said phenyl substituent can be halogen, trifluoromethyl, methyl, methoxy or nitro; and $R^2$ when taken separately is $C_{1-8}$ alkyl, $C_{1-6}$ haloalkyl, $C_{2-6}$ alkenyl, $C_{3-10}$ cycloalkyl $C_{3-10}$ cycloalkyl-$C_{1-6}$ alkyl, $C_{1-4}$ alkoxycarbonyl-$C_{1-8}$ alkyl, $C_{2-8}$ carboxyalkyl, phenyl, phenyl-$C_{1-6}$ alkyl, phenyl-$C_{2-6}$ alkenyl, substituted phenyl, substituted phenyl-$C_{1-6}$ alkyl or substituted phenyl $C_{2-6}$ alkenyl wherein the said substituent can be halogen, trifluoromethyl, methyl, methoxy or nitro or $R^1$ and $R^2$ together form a lactam ring having 5 to 7 ring atoms.

4. The method of claim 1 wherein an amount of a compound of formula (I) effective to alleviate asthma is administered,

 (I)

wherein Ar represents a triazolyl group substituted by one or two radicals selected from the group consisting of $C_{1-4}$ alkyl and phenyl, the acylamino group —$NR^1COR^2$ being attached to a carbon atom of the heteroaryl ring, $R^1$ is selected from the group consisting of $C_{1-6}$ alkyl, benzyl and benzyl substituted by halogen; and $R^2$ is selected from the group consisting of $C_{1-8}$ alkyl, $C_{3-8}$ cycloalkyl, phenyl, and benzyl.

* * * * *

UNITED STATES PATENT AND TRADEMARK OFFICE
CERTIFICATE OF CORRECTION

PATENT NO. : 4,089,962

DATED : May 16, 1978

INVENTOR(S) : Roger Garrick Harrison et al.

It is certified that error appears in the above-identified patent and that said Letters Patent are hereby corrected as shown below:

Column 2, line 17, "$-C\overset{=}{\cdot}$" should read -- $-C=$ --.

Column 5, line 7, "pheny" should read -- phenyl --; line 19, "5methylamino" should read -- 5-methylamino --.

Column 8, line 6, "1-phenyl-1-phenyl-1(H)-1,2,3-" should read -- 1-phenyl-1(H)-1,2,3- --; line 7, "trizole)." should read -- triazole). --.

Column 9, line 26, "dixoide" should read -- dioxide --.

Column 11, line 11, there should be a comma after "$C_{3-6}$ alkenyl"; line 20, "phenyl-$C_{2-}$" should read -- phenyl-$C_{2-6}$ --; line 21, remove the first "6".

Column 12, line 26, "phenyl-$C_{2-}$" should read -- phenyl-$C_{2-6}$ --; line 27, remove the first "6".

Signed and Sealed this

Twenty-second Day of May 1979

[SEAL]

Attest:

RUTH C. MASON
Attesting Officer

DONALD W. BANNER
Commissioner of Patents and Trademarks